(12) United States Patent
Kallen

(10) Patent No.: US 11,589,788 B2
(45) Date of Patent: Feb. 28, 2023

(54) PREDICTION OF MOOD AND ASSOCIATED OUTCOMES BASED ON CORRELATION OF AUTONOMOUS AND ENDOCRINE PARAMETERS

(71) Applicant: NEDERLANDSE ORGANISATIE VOOR TOEGEPAST- NATUURW- ETENSCHAPPELIJK ONDERZOEK TNO, 's-Gravenhage (NL)

(72) Inventor: Victor Louis Kallen, Amsterdam (NL)

(73) Assignee: NEDERLANDSE ORGANISATIE VOOR TOEGEPAST- NATUURW- ETENSCHAPPELIJK ONDERZOEK TNO, 's-Gravenhage (NL)

( * ) Notice: Subject to any disclaimer, the term of this patent is extended or adjusted under 35 U.S.C. 154(b) by 318 days.

(21) Appl. No.: 16/625,911

(22) PCT Filed: Jun. 29, 2018

(86) PCT No.: PCT/NL2018/050423
§ 371 (c)(1),
(2) Date: Dec. 23, 2019

(87) PCT Pub. No.: WO2019/004833
PCT Pub. Date: Jan. 3, 2019

(65) Prior Publication Data
US 2020/0163606 A1    May 28, 2020

(30) Foreign Application Priority Data
Jun. 30, 2017   (EP) .................................. 17179115.5

(51) Int. Cl.
*A61B 5/16*   (2006.01)
*G16H 50/30*   (2018.01)
(Continued)

(52) U.S. Cl.
CPC .............. *A61B 5/165* (2013.01); *A61B 3/112* (2013.01); *A61B 5/02055* (2013.01);
(Continued)

(58) Field of Classification Search
None
See application file for complete search history.

(56) References Cited

U.S. PATENT DOCUMENTS

| | | | |
|---|---|---|---|
| 2011/0306845 A1 | 12/2011 | Osorio | |
| 2014/0288401 A1* | 9/2014 | Ouwerkerk | .......... A61B 5/7225 600/345 |
| 2016/0029939 A1 | 2/2016 | Ouwerkerk et al. | |

FOREIGN PATENT DOCUMENTS

WO    2013/076615 A1    5/2013

OTHER PUBLICATIONS

Young et al. (We should be using nonlinear indices when relating heart-rate dynamics to cognition and mood; 2015; Scientific Reports | 5:16619 | DOI: 10.1038/srep16619) (Year: 2015).*

(Continued)

*Primary Examiner* — Jay B Shah
(74) *Attorney, Agent, or Firm* — Lucas & Mercanti, LLP

(57) ABSTRACT

The present invention relates to a method to predict the risk of obtaining a stress related mood disorder or syndrome by a person, comprising a. Measuring at least three parameters comprising at least one sympathetic, one parasympathetic and one hormonal parameter during a stress response, said result of the measurement depicted as RS, RP and RH respectively; b. Estimate the value of one of these parameters by calculating it from the other two parameters; c. Predict the risk on basis of the deviation between calculated and measured value of the parameter that has been estimated in step b).

22 Claims, 6 Drawing Sheets

Figure 1:
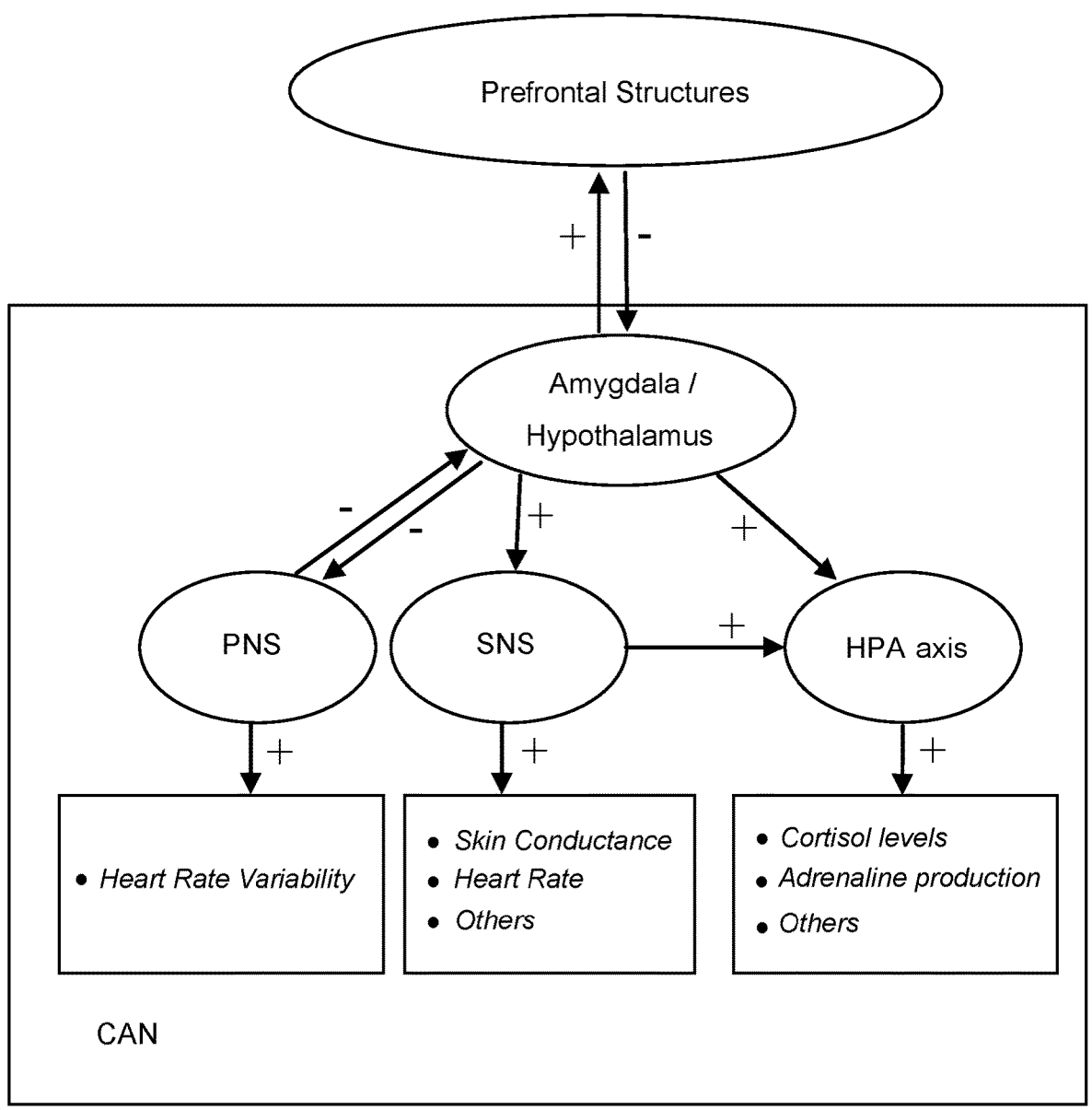

(51) Int. Cl.
*A61B 3/11* (2006.01)
*A61B 5/0205* (2006.01)
*A61B 5/145* (2006.01)
*A61B 5/1455* (2006.01)
*A61B 5/00* (2006.01)
*A61B 5/021* (2006.01)
*A61B 5/024* (2006.01)
*A61B 5/053* (2021.01)

(52) U.S. Cl.
CPC ........ *A61B 5/1455* (2013.01); *A61B 5/14546* (2013.01); *A61B 5/4884* (2013.01); *A61B 5/681* (2013.01); *A61B 5/7246* (2013.01); *A61B 5/7275* (2013.01); *A61B 5/742* (2013.01); *G16H 50/30* (2018.01); *A61B 5/021* (2013.01); *A61B 5/02405* (2013.01); *A61B 5/053* (2013.01); *A61B 2560/0214* (2013.01); *A61B 2562/0215* (2017.08); *A61B 2562/0219* (2013.01)

(56) References Cited

OTHER PUBLICATIONS

International Search Report and Written Opinion for Corresponding International Application No. PCT/NL2018/050423 (13 Pages) (dated Oct. 15, 2018).

\* cited by examiner

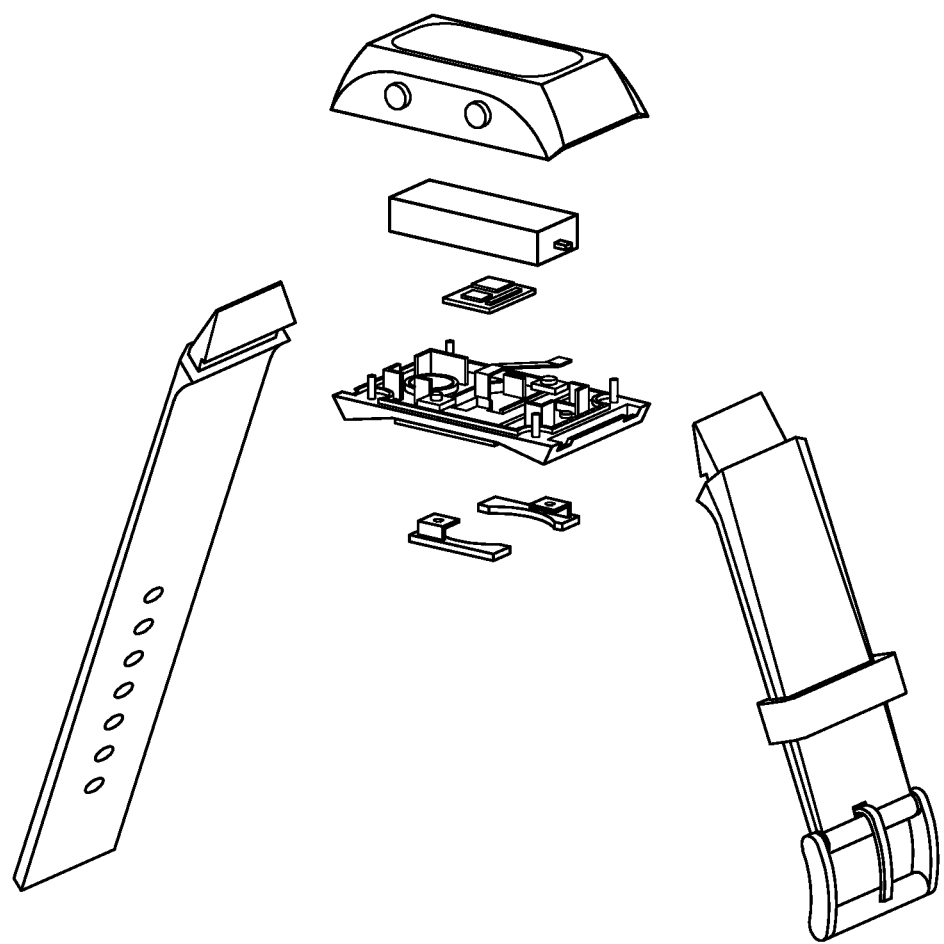
Fig. 6
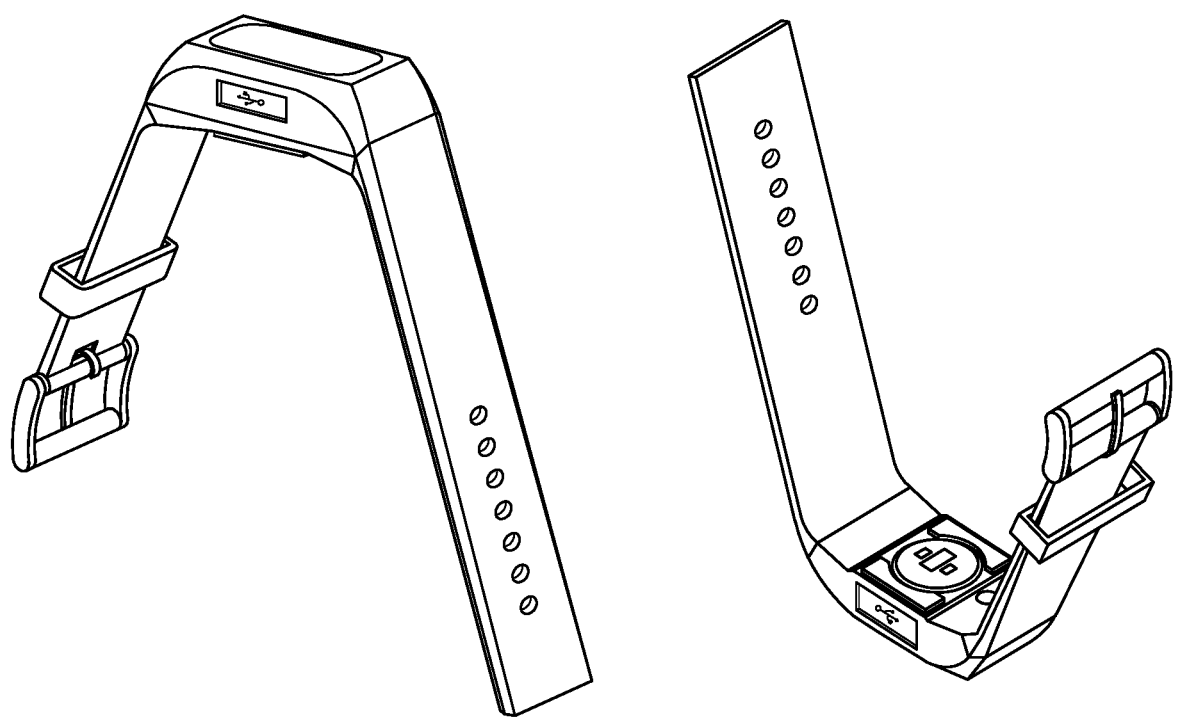

PREDICTION OF MOOD AND ASSOCIATED OUTCOMES BASED ON CORRELATION OF AUTONOMOUS AND ENDOCRINE PARAMETERS

CROSS-REFERENCE TO RELATED APPLICATIONS

This application is a 371 of PCT/NL2018/050423, filed Jun. 29, 2018, which claims the benefit of European Patent Application No. 17179115.5, filed Jun. 30, 2017.

FIELD OF THE INVENTION

The invention relates to the prediction of mood, more in particular responsiveness to stress, more in particular stress related anxiety, on basis of a correlation between simple measurements of autonomous and endocrine parameters.

BACKGROUND

The (human) body has a built-in automatic emergency response that uses the Autonomous Nervous System (ANS) and endocrine systems, most prominently the Hypothalamus—Pituitary Gland—Adrenal gland (HPA)—axis, to enhance the body's performance when danger is perceived. When the body is healthy and functioning normally, this is reflected in both a homeostatic and heterostatic state: both within the ANS and the endocrine systems involved, a natural balance is at place, or in response to stress, causing some temporarily disturbances, quickly returned to (homeostasis). When external pressure is significant, responses of both systems are aligned for a short/necessary period of time, and when the stress is relieved, they return to their original heterostatic ('independently operating') state.

When danger is perceived, both the ANS and hormonal systems automatically change the body's balance by producing a "stress response" (also called the "emergency response," the "fear response," or the "fight or flight response."). This change of balance—focusing attention and emergency readiness—is initiated via an ANS response, immediately followed by the production of hormones—chemical messengers that are secreted into the bloodstream (like, though not exclusively, (nor)epinephrine or corticotrophin releasing hormone (CRH)). Some of these endogenously induced changes can be measured and quantified.

The moment danger is perceived the ANS is activated (generally causing activation of the sympathetic nervous system and inhibition of the parasympathetic nervous system) and neurotransmitters and hormones ((nor)epinephrine, cortisol, others) are secreted, e.g. into the bloodstream to bring about specific physiological, psychological, and emotional changes that enhance the body's ability to deal with the threat. In this way the stress response causes many physiological, psychological, and emotional changes, such as it:

Energizes the body/heightened glucose metabolism;
Heightens our awareness of and reaction to danger (increases focus & concentration; alertness; vigilance);
Elevates heart rate, decreases Inter Beat Interval (IBI) times;
Decreases Heart Rate Variability (parasympathetic tonus via the nervus vagus;
Changes breathing and/or elevates breathing frequency and efficiency (opening bronchi in the lungs);
Stimulates the nervous system;
Tightens muscles;
Suppresses digestion and appetite;
Changes stomach and digestive function;
Alters nutritional needs/metabolic state/dietary preferences and habits;
Changes brain functioning;
Constricts blood vessels;
Changes blood flow;
Stimulates sweat production thus increasing skin conductance and decreasing skin resistance
and many more.

As 'stress' is elicited by a discrete set of stimuli, and the stress responses are executed by a discrete set of effectors. These responses occur in a multidimensional continuum: all organic systems involved react ranging from subtle to significant. The responses can be measured or assessed and are all in one way or another associated with either the severity of the occurring stressor and/or the individual sensitivity or proneness for stress in general. More specifically, a tremendous exogenous stressor will elicit a series of well assessable ANS and endocrine responses in (almost) all individuals, whereas more subtle stressors only trigger measurable (interactive) responses in individuals with a higher stress sensitivity. And vice versa: heightened stress sensitivity and proneness for mid-to long term stress related health outcomes can thus be established by assessing whether and/or to what extent particular and well defined combinations of stress responses in the ANS and endocrine systems are present in any given individual. This is a significant step forward, as normally the degree of stress response, within either the ANS and/or the endocrine systems (independently), is considered to be directly proportional to the degree of perceived danger, an assumption widely (though not necessarily always 'accurately') applied as presumed (valid) quantification of 'stress'.

Consequently, extensive, impactful stressors can be identified (and even 'quantified') objectively when ANS and endocrine response align themselves in one 'heterostatic' dynamic response. Typically, this condition will be reached significantly earlier with heightened anxiety traits in any given individual, with the most profound profile being found in individuals suffering from stress related pathology like burn-out, depression and/or anxiety (disorders) or trauma. Under such circumstances of an emerging severe threat and/or strengthened by the presence of, pathological conditions (anxiety disorders and the like), the ANS and endocrine response patterns will become highly associated and show (measurable/quantifiable) reciprocal dynamics.

It has been established that both genetic predispositions and life time (traumatizing) experiences contribute to the phenotypical sensitivity of both domains involved independently and thus to the proneness for anxiety or stress related outcomes in general (like burn-out anxiety disorders, for example Post Traumatic Stress Disorder, others), and to the currently identified/described heterostatic dynamics more specifically. With the latter being a more accurate marker of emotional state and/or trait as compared to both components (ANS functioning and endocrine dynamics) independently.

Diagnosis of anxiety disorders and associated syndromes (e.g. burn-out, depression) hitherto has been typically achieved by standardized and validated clinical questionnaires such as the Taylor Manifest Anxiety Scale, The Beck Depression Inventory (BDI) the Social Anxiety Scale for Adolescents, and/or The State and Trait Anxiety Inventory (STAT).

Also prediction of susceptibility for chronic or severe anxiety related disorders has hitherto been based on psychological parameters. It has been suggested that for example neuroticism would be a good predictor for the development of anxiety disorders in adolescents (Zinbarg, R. E. et al., 2016, Clin. Psychol. Sci., doi: 10.1177/2167702615618162). However, molecular genetics, physiological responsiveness to stress, and/or biochemistry have so far failed to identify variation(s) that are consistently associated with the increased psychologically measurable susceptibility to stress and/or anxiety feelings in generally (yet) healthy subjects. Consequently, an adequate method to quantify stress, preferably in terms of the associated risk to develop lasting anxiety related outcomes, and/or associated somatic mid to long term health consequences, is yet lacking. Accordingly, a simple and objective test for the quantification and prediction of (susceptibility for) anxiety and associated outcomes is still needed.

SUMMARY OF THE INVENTION

The present inventors now have found that it is possible to predict the risk of obtaining a stress related mood disorder or syndrome by a person, by a method comprising
   a. Measuring at least three parameters comprising at least one sympathetic, one parasympathetic and one hormonal parameter during a stress response, said result of the measurement depicted as $R^s$, $R_p$ and $R^h$ respectively;
   b. Estimate the value of one of these parameters by calculating it from the other two parameters;
   c. Predict the risk on basis of the deviation between calculated and measured value of the parameter that has been estimated in step b).

Preferably the measurement during a stress response in step a) is performed according to a method comprising the steps of
   a. measuring during rest condition at least three parameters, comprising at least one sympathetic parameter, said parameter being a parameter related to the sympathetic autonomous nerve system ($S_1^{rest} \ldots S_n^{rest}$, in which n is the number of parameters), at least one parasympathetic parameter, said parameter being related to the parasympathetic autonomous nerve system ($P_1^{rest} \ldots P_n^{rest}$, in which n is the number of parameters) and at least one hormonal parameter, said parameter being related to the hormonal system of the hypothalamus-pituitary gland—adrenal (HPA) axis ($H_1^{rest} \ldots H_n^{rest}$, in which n is the number of parameters);
   b. applying a stress stimulus resulting in a stress condition;
   c. measuring said at least three parameters measured in step a) during the stress condition ($S_1^{stress} \ldots S_n^{stress}$; $P_1^{stress} \ldots P_n^{stress}$; $H_1^{stress} \ldots H_n^{stress}$;)
   d. calculate the stress response of each parameter by taking the ratio or difference between the values measured in step a) and the values measured in step c): $R^s_{1..n}=S_1^{stress}/S_1^{rest} \ldots S_n^{stress}/S_n^{rest}$, $R^p_{1..n}=P_1^{stress}/P_1^{rest} \ldots p_n^{stress}/P_n^{rest}$, $R^h_{1..n}=H_1^{stress}/H_1^{rest} \ldots H_n^{stress}/H_n^{rest}$.

Also part of the invention is a method as defined above, wherein the estimation in step b) is achieved by a method comprising the steps of
   a. comparing the values of two of said at least three measured parameters with averaged data taken from a normal control group to find values that closely resemble the values measured;
   b. taking the value of the third parameters that belongs to the averaged normal control data as the estimated value of the third parameter.

Preferably, in said method the normal control group is chosen to be representative for the person tested, preferably wherein the person and/or the control group are not adolescents.

Further part of the invention is a method as defined above, wherein the parameter which is estimated is the hormonal parameter.

Further part of the invention is a method as defined above, wherein the stress stimulus is a standardized stress stimulus.

In a further preferred embodiment the at least one parameter relating to the sympathetic autonomous nerve system is chosen from the group consisting of Skin Conductance (SC), pupil dilatation, and specified derivatives of blood pressure, such as low/mid frequency power, reflecting changes over time in frequencies between 0.7 and 0.15 Hz, of Systolic Blood Pressure.

Also part of the invention is an embodiment, wherein the at least one parameter relating to the parasympathetic autonomous nerve system is chosen from the group consisting of heart rate derivatives, such as Inter Beat Interval derived Heart Rate Variability (HRV), quantifiable as the root Mean Square of Successive interbeat-interval Differences (RMSSD), or the High Frequency power of the Heart Rate power spectrum.

In a further preferred embodiment the at least one hormonal parameter is chosen from the group consisting of the concentration of said person of cortisol, ACTH, CRF, vasopressin or adrenalin in a saliva, blood or urine sample, or via the skin or optical methods.

Also part of the invention is a method for continuously assessing the stress level of a person, comprising:
   a. Continuously or intermittently measuring at least two parameters comprising at least one sympathetic and at least one parasympathetic parameter;
   b. Estimating the value of the hormonal parameter from the values measured in step a).

Preferably said method is used to detect stressful events and/or said method is used to predict if said person is suffering from a stress related mood disorder or syndrome. In another embodiment said method is used to monitor the effect of a treatment for a person suffering from a stress related mood disorder or syndrome.

Further part of the invention is a method according to the invention, wherein the stress related mood disorder or syndrome is anxiety, depression, more specifically bipolar disorder or major depressive disorder, insomnia, posttraumatic stress disorder, obsessive-compulsive disorder, chronic fatigue syndrome, burn-out, chronic fatigue syndrome, fibromyalgia, irritable bowel syndrome or substance use disorders, preferably anxiety.

The invention further comprises a system comprising one or more devices for measurement of at least two parameters selected from at least one sympathetic parameter, at least one parasympathetic parameter and one hormonal parameter, further comprising a unit able to process an algorithm for performing a method as defined above. Preferably said device(s) are able to measure at least one of heart rate and/or derivatives like Heart Rate Variability (HRV), blood pressure, breathing rhythm, concentration of cortisol, ACTH, CRF, adrenalin or vasopressin. In a specially preferred embodiment said system is a portable system, preferably a wristwatch. In a further preferred embodiment said system has an output means, preferably a screen. In another embodiment said system comprises a storage means for storing of the measured data. It is also possible that said measurement devices and said unit are remote from each other and these are able to communicate data or instructions. In a further embodiment the unit for processing the algorithm and at least one measuring device are housed in the same housing.

LEGENDS TO THE FIGURES

FIG. 1. Schematic view of the CAN: Central Autonomous Network and its implications for peripheral physiological responses. Structures like the amygdala and the hypothalamus inhibit the Parasympathetic Nervous System (PNS) resulting in lowered Heart Rate Variability, and stimulate the Sympathetic Nervous System (SNS) increasing Skin Conductance and Heart Rate. Additionally, nuclei of hypothalamus stimulate the pituitary gland to produce Adreno-Corticotropic Hormone (ACTH) which stimulates the adrenal glands to produce cortisol: the so called HPA-axis. A loss of central (amygdala) control, possibly due to reduced prefrontal inhibitory influence, may thus result in an overstimulation of the SNS and the HPA-axis simultaneous with a loss of parasympathetic cardiac control. This systemic disturbance is typical for individuals suffering from (psychological) stress.

Figure 2:
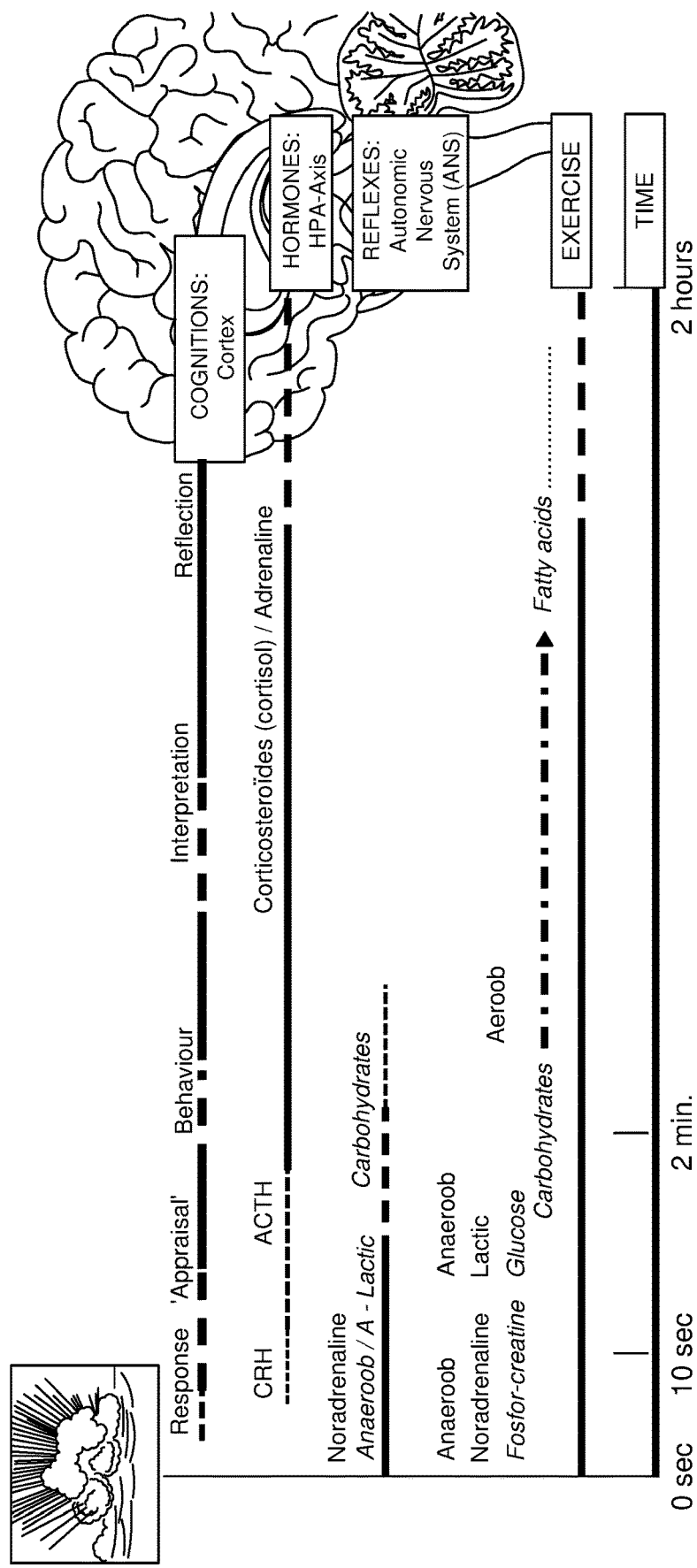

FIG. 2: The stress responses developing over time after an exogenous, stressor. The Autonomic Nervous System (ANS) reacts immediately, and the Hypothalamus—Pituitary Gland—Adrenaline (HPA) axis needs more time to produce sufficient/measurable/quantifiable concentrations of hormones (blue line). If the stressor was only short lasting or mild, a significant hormonal response will not develop, unless the given individual suffers (either diagnosed or not) from a stress related condition like an anxiety disorder or burn-out and is consequently highly sensitive for stress.

Figure 3:
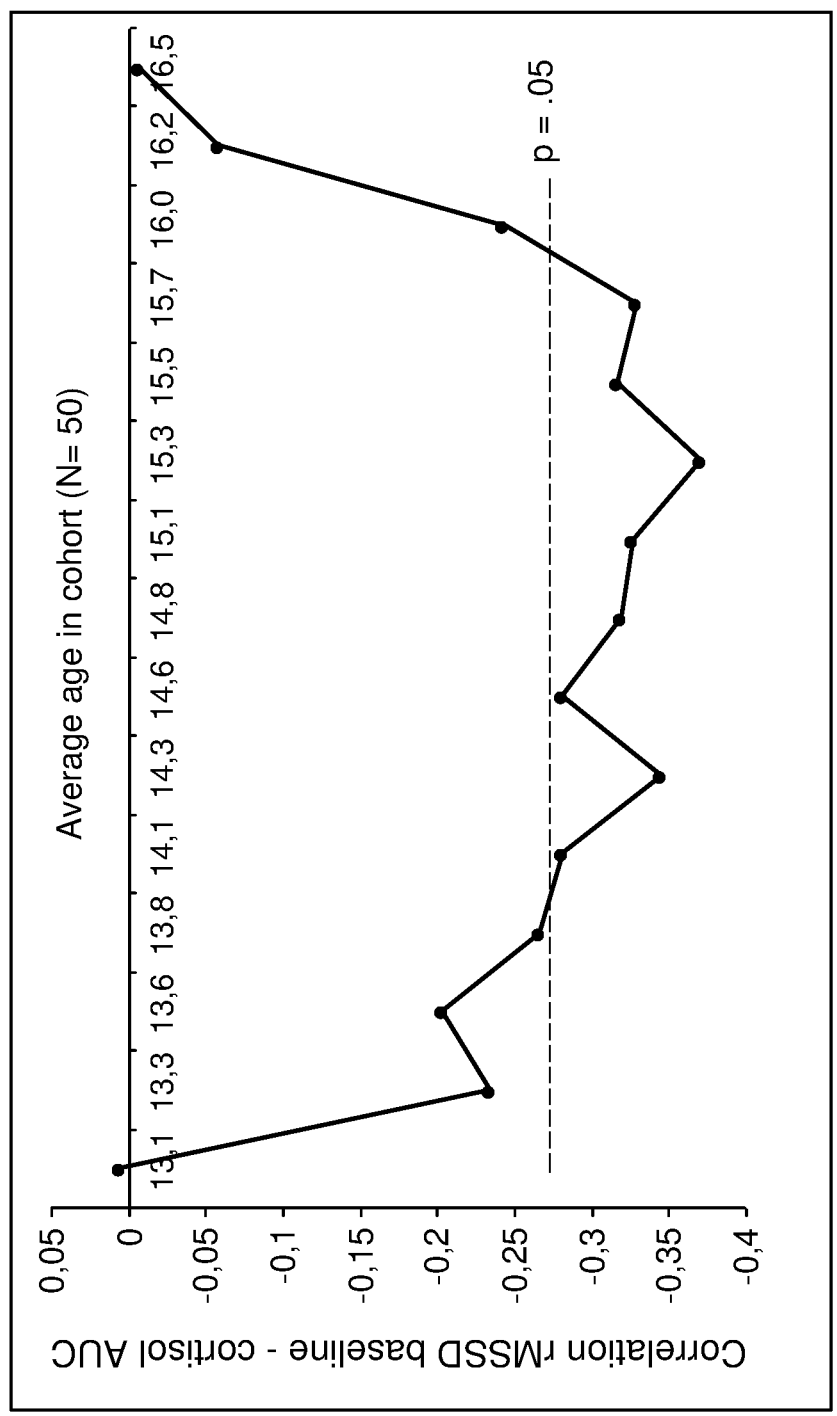

FIG. 3: The typical development of ANS and endocrine correlations in response to stress through adolescence: the dotted line indicates statistical relevance, stating that due to neurophysiological development adolescents seem to be prone for a period of time for a heightened significant stress sensitivity. Consequently, results of assessments with the present invention in adolescents should be interpreted with caution.

Figure 4:
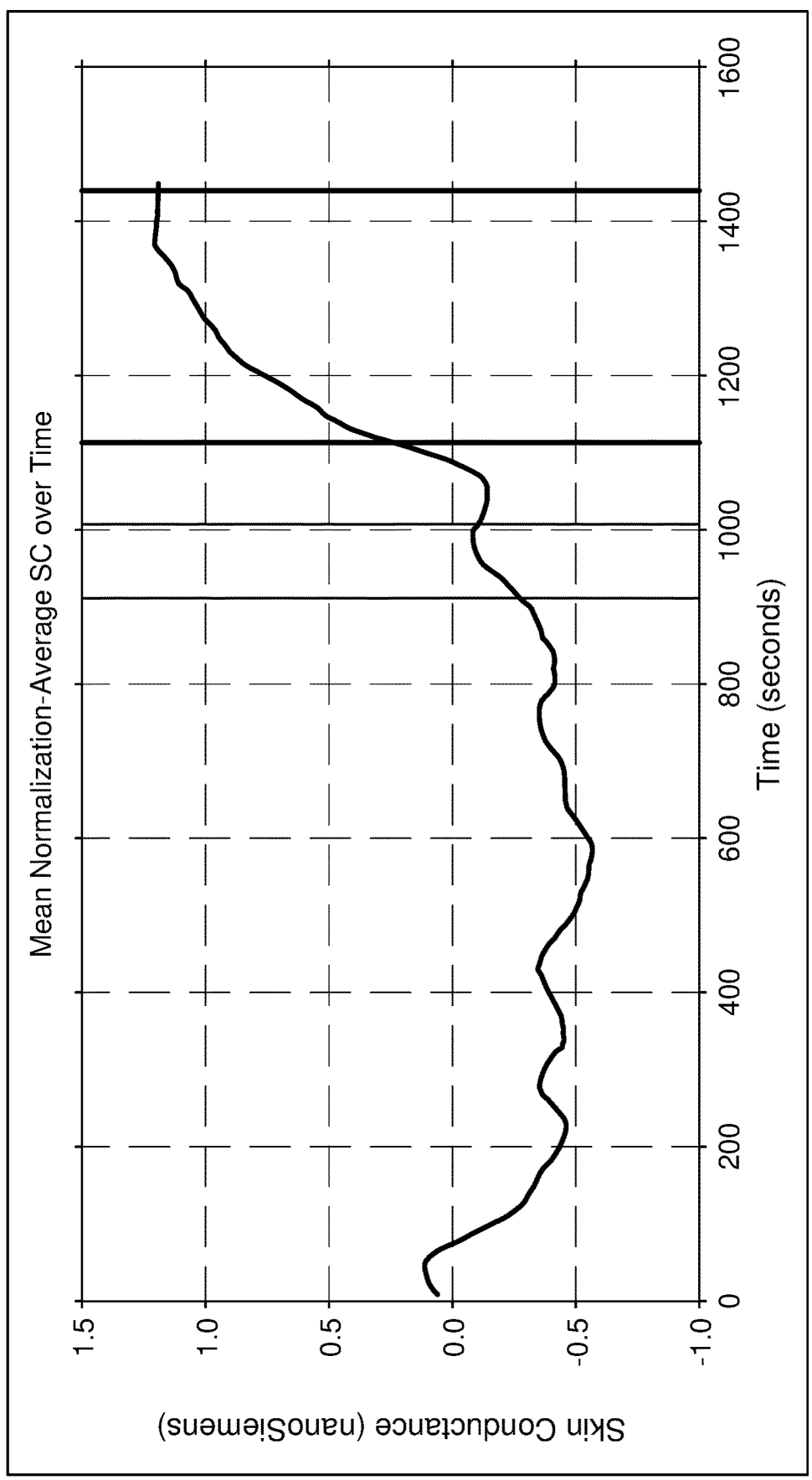

FIG. 4: Mean normalized, average Skin Conductance signal for all test persons (see Example 1)

Figure 5:
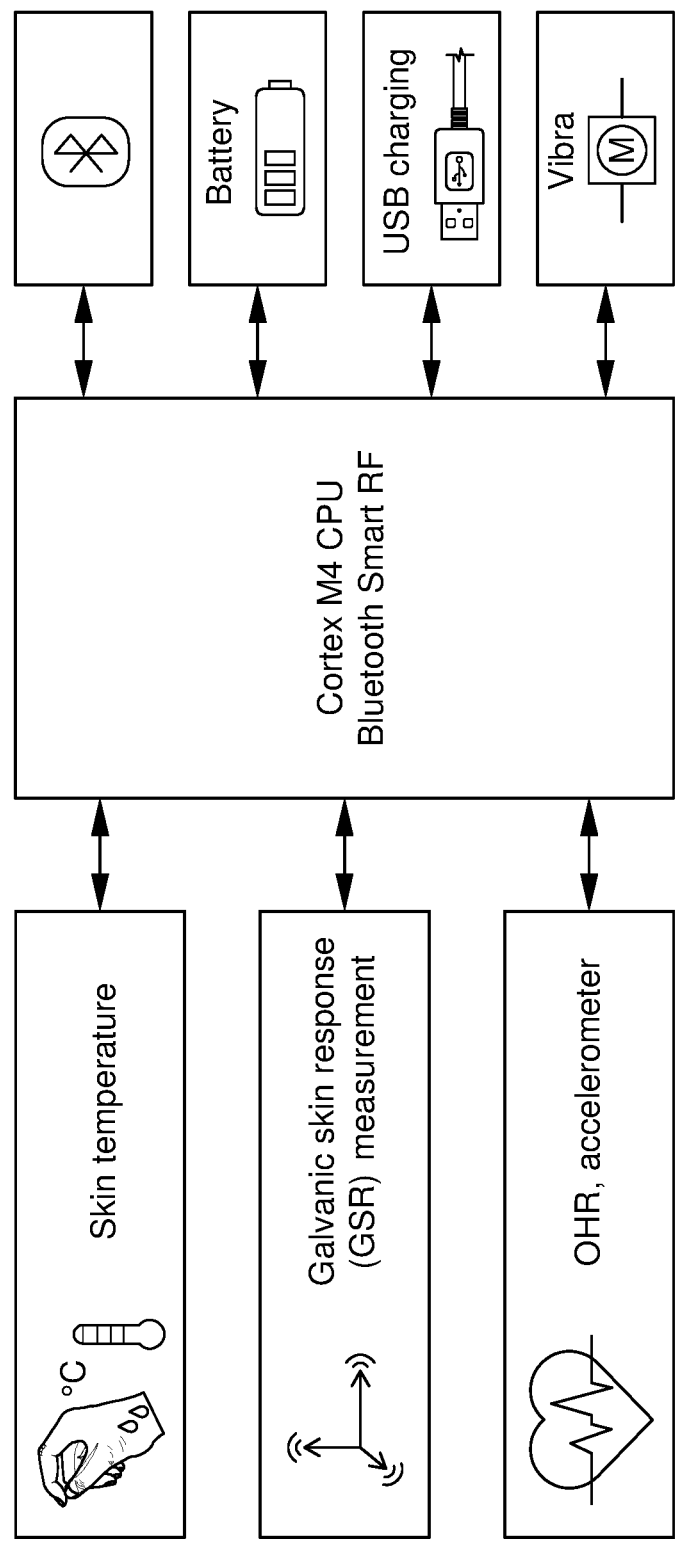

FIG. 5: Functional scheme of a wristwatch according to the invention.

FIG. 6: Schematic construction view and top and bottom view of the design of a wristwatch.

DEFINITIONS

A "physiological parameter" as used in the present invention is a sympathetic, parasympathetic, or combined ('autonomic balance') parameter.

"A sympathetic parameter" as used in the present invention is a physiologic parameter that relates to the sympathetic part of the autonomous nervous system. Examples of sympathetic parameters are Skin Conductance (SC), pupil dilution, and specified derivatives of blood pressure (e.g. low/mid frequency power, reflecting changes over time in frequencies between 0.7 and 0.15 Hz, of Systolic Blood Pressure e.g. in response to a stressor). Estimates of sympathetic activity are sometimes used, which are generally based on dividing a parameter influenced by both sympathetic and parasympathetic by a specified parasympathetic component. E.g. using two Heart Rate Variability components (SDNN and RMSSD) to calculate an estimate sympathetic contribution (SDNN is the standard deviation of NN (beat-to-beat) intervals. SDNN reflects all the cyclic components responsible for variability in the period of recording, therefore it represents total variability. It can be regarded as sympathetic parameter by dividing it with the parasympathetic parameter RMSSD, the square root of the mean of the squares of the successive differences between adjacent NNs). It must be noted that, although sometimes preferred for pragmatic reasons (e.g. only on type of sensor and signal processing procedures necessary to calculate), such estimated parameters are by default less accurate then straightforward sympathetic parameters like mentioned above. The latter should be regarded as the preferred option(s) for the present invention.

"A parasympathetic parameter" as used in the present invention is a physiologic parameter that relates to the parasympathetic autonomous nervous system, which is generally intervened by activation of the nervus vagus. Examples of parasympathetic parameters are heart rate derivatives like Inter Beat Interval derived Heart Rate Variability (HRV). High frequency (beat-to-beat) changes in heart rate are generally considered to be a reliable marker of parasympathetic activity (preferably corrected for breathing: Respiratory Sinus Arrhythmia, RSA) influences). Means to quantify these are many (either time or frequency domain) though generally accepted parameters are for example the Root Mean Square of Successive interbeat-interval Differences (RMSSD: time domain), or the High Frequency power of the Heart Rate power spectrum (frequency domain: beat-to-beat changes with a temporal dynamics of >0.15 Hz), preferably though not necessarily corrected for respiration disturbances (RSA, via mechanical pressure on the thorax/heart). The most straightforward method to circumvent such breathing disturbances during the assessment of HRV is paced breathing (rhythmically in- and exhaling), if reasonably possible in slow wave, mid frequency (0.07-0.15 Hz) ranges ('yoga breathing'). Applying such strategies makes the assessment of parasympathetic activity considerably more reliable.

Parameters combining sympathetic and parasympathetic impetus represent the net outcome of the parallel activities of both neurological trajectories. They are typically referred to as indicating 'Autonomic Balance'. A famous combined parameter is Heart Rate (HR), which is intervened by both trajectories. HR consequently represents the relative contribution of both: if sympathetic signals dominate parasympathetic signals HR increases, if vice versa HR decreases.

"An endocrine or hormonal or HPA parameter" is a measure for the concentration of a specified hormone, most prominently of the hypothalamic-pituitary-adrenal (HPA) axis. Examples of such hormones are cortisol, adrenocorticotropic hormone (ACTH), corticotropin releasing factor or hormone (CRF or CRH), and vasopressin, among others. Other hormones, such as epinephrine and oxytocin, may also be used in the present invention "A resting condition" as used in the present invention is the situation of the body in rest, i.e. only providing basal physiologic functions. An appropriate measurement of a 'baseline' or resting condition as used herein may be obtained by sitting or lying for 5 or more minutes without performing a physical or mental task.

"A stressing condition" as used herein is the condition after sufficient exposure to a stress stimulus. A stress stimulus may be a physical exercise (such as running, jogging, exercising on a fitness apparatus, etc.), or a mentally challenging task (like a presentation for an audience, heated discussions, mental arithmetic tasks or other professional cognitive challenges). If a stress stimulus is of significant severity or duration, or a given individual is sensitive for stress (for example in case of an anxiety disorder like a panic disorder) a (stress) response is initiated, which is defined a significant and simultaneous increase in sympathetic activity and decrease in parasympathetic tonus immediately following the stress stimulus.

A stress response can for example be quantified by a net change of at least 10%, preferably at least 15%, more preferably at least 20%, more preferably at least 25%, more preferably at least 30% in a physiologic parameter, such as heart rate and/or inter beat intervals (IBI's). Further, a significant increase of sympathetic activity be quantified by using multiple different parameters, for example by an increase in skin conductance, preferably more than 25% increase, more preferably more than 30%. A significant decrease in parasympathetic tonus can be quantified using diverse parameters, though for example by a reduction of any component of heart rate variability, possible to assess by various means, such as the root mean square successive difference (RMSSD) of consecutive inter beat intervals (IBI's) over a defined period of number of heart beats; or the high frequency power of the IBI derivate power spectrum in comparison to the rest condition.

If this dynamic (ANS) phenomenon is present in response to an exogenous source and it is followed by a significant hormonal increase (of at least 20 to 30% (e.g. 3 to 3.7 or more, or 8 to 11.2 nmol/l for cortisol in saliva) within approximately 10 to 15 minutes after this physiological stress response), the exogenous source can be identified as a significant 'stressor' and/or the tested individual is oversensitive for the applied stressor. Also, if it can be established that such response patterns occur regularly and/or even to relative mild stressors the given individual can be quantified as 'vigilant' or 'sensitive' what may be highly indicative for (the development towards) anxiety and stress related conditions Stress is in this way defined as:
A. The impact of an exogenous source, causing disturbances in multiple physiological domains that can be associated with both the source and each other.
B. Providing (via these combined, associated and reciprocal reactions) consequences for mid to long term recovery and health (either psychological or physical).
C. On a physiological level it is characterized by a measurably increase in (HPA-axis associated) hormones following an dynamic ANS response (generally mirrored in an increase in sympathetic activity combined with a decrease in parasympathetic activity).

In individuals that are prone to stress or anxiety related outcomes (like anxiety disorders, depressions, burn-out) this stress response or stress condition will typically and generally be present, even in response to only mild stressors or challenges. In mentally healthy individuals the reciprocal dynamics between the ANS and HPA-axis in response to day to day stress is generally absent (unless the stressor becomes objectively significantly severe). An exception here are adolescent humans (aged 12 to 18 years who as a result of the changes in their developing neurophysiology can be regarded to be in a constant stress situation (see FIG. 3). Consequently, when persons of the age 12-18 are being tested extreme care should be taken to take matching control subjects. In elderly specific dynamic changes may develop within the hormonal domain (age proportion corticosteroids vs DHEA), though generally speaking that will not affect the—for this invention to be assessed—interactions with the ANS parameters.

For this reason it is advantageous to use age-matched controls.

The stress response and/or state can typically be measured if an exogenous stressor causes a stress condition lasting at least 5 and less than 45 minutes. Shorter lasting stressors generally only cause 'startle responses' (short during ANS response as described previously); producing the hormones of the HPA-axis generally takes 5 to 15 minutes; with exhaustion gradually developing as from 20 minutes onwards (see FIG. 2).

A "stress related mood disorder", "stress related mood syndrome" or "stress related disease" as used in the present invention is any mood disorder or functional illness that is known to be related to activation of the HPA axis. These include anxiety or anxiety disorder, depression, more specifically bipolar disorder or major depressive disorder, insomnia, posttraumatic stress syndromes like for example Post Traumatic Stress Disorders (PTSD), obsessive-compulsive disorder (OCD), burnout, chronic fatigue syndrome, fibromyalgia, irritable bowel syndrome and substance use disorders, such as alcoholism.

"Anxiety" or "anxiety disorder" is a mood disorder, defined as a feeling of fear that is out of proportion to the nature of the threat. There are a number of anxiety disorders: including generalized anxiety disorder, specific phobia, social anxiety disorder, separation anxiety disorder, agoraphobia, and panic disorder.

"Susceptibility for a stress related disease" is the status of a person having a high risk, what can be quantified in the proportion of changes in hormonal concentrations that are associated with dynamic responses of the ANS to an exogenous stressor: lower reciprocity being typically associated with lower risk for the (upcoming) development of stress related diseases. (like mood or anxiety disorders) later in life.

DETAILED DESCRIPTION

In the present invention it has thus been established that stress can be defined and even quantified by the extent of the hormonal response of the hypothalamus-pituitary gland—adrenal (HPA) axis following and proportionally related to the response of the Autonomic Nervous System to a stressor or (exogenous) challenge. In more mathematical terms: stress can be defined as the proportion of variance in endocrine responsiveness that is explained by the variance in ANS responsiveness. In the absence of a stressor and/or in normal, control persons, this proportion is low (or even absent, both systems respond 100% independently), when the amount of stress increases or when persons suffer from a stress related disease, this proportion will rise considerable (to statistical significance: both systems reacted homeostatically reciprocal). Thus, the stress response can be quantified (for example) by an increase of approximately or exceeding 25% in cortisol concentrations in a sample (such as blood, saliva or sensors) within 15 minutes following the stress stimulus. "Since the hormonal response, in combination with the response of the autonomous nerve system (both sympathetic and parasympathetic) is strongly related to the risk of obtaining a stress response based mood disorder, this finding opens a perspective for new risk assessment methods and/or stress monitoring technology.

Accordingly, the combined measurement of sympathetic, parasympathetic and endocrine parameters provides for a reliable measure of the severity of (mood) changes on basis of a stress stimulus. As a consequence, the measurement as claimed may be used to predict the risk of the development of a stress response related outcomes, diseases, especially anxiety disorder. The invention thus comprises a method to predict the risk of obtaining a stress related mood disorder or syndrome by a person, comprising a. Measuring at least three parameters comprising at least one sympathetic, one parasympathetic and one hormonal parameter during a stress response, said result of the measurement depicted as $R^s$, $R^p$ and $R^h$ respectively;
b. Estimate the value of one of these parameters by calculating it from the other two parameters;
c. Predict the risk on basis of the deviation between calculated and measured value of the parameter that has been estimated in step b)

The measurement in step a) is performed according to a method comprising the steps of d. measuring during rest condition at least three parameters, comprising at least one sympathetic parameter, said parameter being a parameter related to the sympathetic autonomous nerve system ($S_1^{rest}$ ... $S_n^{rest}$, in which n is the number of parameters), at least one parasympathetic parameter, said parameter being related to the parasympathetic autonomous nerve system ($R_1^{rest}$ ... $P_n^{rest}$, in which n is the number of parameters) and at least one hormonal parameter, said parameter being related to the hormonal system of the hypothalamus-pituitary gland—adrenal (HPA) axis ($H_1^{rest}$ ... $H_n^{rest}$, in which n is the number of parameters);
e. applying a stress stimulus resulting in a stress condition;
f. measuring said at least three parameters measured in step a) during the stress condition ($S_1^{stress}$ ... $S_n^{stress}$; $P_1^{stress}$ ... $R_n^{stress}$; $H_1^{stress}$ ... $H_n^{stress}$;)
g. calculate the stress response of each parameter by taking the ratio or difference between the values measured in step a) and the values measured in step c): $R^s_{1..n}=S_1^{stress}/S_1^{rest}$ ... $S_n^{stress}/S_n^{rest}$, $R^p_{1..n}=P_1^{stress}/P_1^{rest}$ ... $P_n^{stress}/P_n^{rest}$, $R^h_{1..n}=H_1^{stress}/H_1^{rest}$ ... $H_n^{stress}/H_n^{rest}$.

The calculation is step d) is preferably made on the ratio between the values since this is independent of the absolute values.

The measurement itself is simple and may be performed in any clinical or even non-clinical setting. A typical assessment starts with measuring at least three parameters during a resting or baseline condition. These at least three parameters are at least one sympathetic parameter, at least one parasympathetic parameter (together capturing 'autonomic balance') and at least one hormonal parameter The resting condition is obtained by positioning the test person is a sitting or lying condition without performing any physical or mental activity for a sufficiently long time (5 minutes or more) to ensure that the physiologic parameters to be measured have become stable. It should be indicated that applying paced breathing (slow, deep, diaphragmatic breathing) significantly increases the quality of the acquired data using such protocols. Of course this can be achieved by waiting, but a more reliable indication is obtained when all the physiologic parameters (or at least the sympathetic and parasympathetic parameters) become relatively stable, when measured continuously. It is also possible to take more than one measurement during the rest period (also in the case of continuous measuring the parameter(s), a value may be taken at different time moments during the resting condition) and to average the measurements. It is envisaged that by averaging the measurement a more reliable value may be obtained.

It must be mentioned that many endocrine/hormonal systems follow a circadian rhythm by phasic changes over the day concentrations may be naturally higher in the morning (like in the HPA-axis) as compared to the evening or at night. This means that measurements in the afternoon or (early) evening are preferred for reliably assessing a stress response from the HPA-axis. To the contrary, accurate parasympathetic baseline values can typically (or best) (though not necessarily) be measured while either sleeping or shortly after awakening (preferably still in supine position).

However, more protocolled measurements (using a standardized baseline as described above) can very well be used. When such baseline measurements are taken these are indicated as 'rest'-values. In the present application these are denoted as $S^{rest}$, $P^{rest}$, $H^{rest}$, where S, P and H identify a Sympathetic, Parasympathetic and Hormonal (or endocrine) parameter, respectively. Since there can be more than one parameter of each category, in this notation these parameters then would receive a number: $S_1^{rest}$, $S_2^{rest}$, to $S_n^{rest}$ ... for the n-th sympathetic parameter. Of course the same principle applies to parasympathetic and hormonal parameters.

After obtaining the rest value, a stress stimulus is applied. This may be any stimulus that is capable of generating a stress response. The stimulus may be a psychological/emotion inducing stimulus, but it may also be a physical stimulus. Physical stimuli can for instance be the performing of a physical exercise, such as running, jogging, gymnastics (e.g. push-ups), rope jumping, etc. Psychological stimuli may be tasks that are perceived as being stressful, such as an interview, a lecture before an audience, mental arithmetic (either or not under (time) pressure), writing an exam, cognitive challenges, etc. The stress stimulus, if applied for a sufficient severity and sufficient amount of time will lead to a stress condition. This stress condition is defined relative to the rest condition, since the characteristics (and the values of the parameters) of the rest condition and the stress condition will vary from person to person. In general the stress condition will lead to a change in the physiology of respiration, blood circulation and hormonal balance (to enable the 'flight or fight' response) that will peak sometime after the stress condition has been achieved. The intention is that a sequential measurement (after the initial baseline, resting state, measurement) is made on the rising slope or even preferably the maximum of the post stressor increase (or decrease in case of parasympathetic inhibition). The sympathetic and parasympathetic parameters will respond relatively immediately, though the endocrine response will meet with some delay (typically 'minutes'), which is due to the sequential synthesis of relevant molecules (see FIG. 2).

Consequently, when any given individual has reached the stress condition in such a way that it may be assumed that the physical parameters are sufficiently influenced by the stress condition, the parameters that have been measured during the rest condition are now again measured. Similar to the rest condition, these parameters are now noted as $S^{stress}$, $P^{stress}$, and $H^{stress}$. Again, similar to the measurements taken in the rest condition the measurements may be taken continuously or repeatedly and the results may be obtained by e.g. averaging multiple measurements, or selecting the highest in- or decrease as compared to the baseline measurement, as specific timing of the maximum is hard to predict precisely. However, in the latter case, care should be taken not to wait too long between the individual measurements that will be averaged. Time windows for optimal measurements are typically defined in second or minute ranges following a (presumed) stressor Additionally to the above mentioned methodologies, a well known and commonly used parameter of endocrine/hormonal stress reactivity (e.g. in research environments) is the cumulative 'Area under the Curve' (AUC) measurement. AUC can be regarded as the calculation of one gross-estimator of an endocrine response to a stressor by adding up all post stressor hormonal values, either related to the 'ground' (zero values as baseline) or to the increase (a baseline drawn from the lowest pre-stress concentrations to the lowest post stress concentrations). This presents one overall value for hormonal reactivity ('$H^{stress}$'), which can be regarded representative and can advantageously consequently be used in the presented methodology (see Preussner, J. C., Kirschbaum, C., Meinlschmid, G., and Hellhammer, D. H. *Psychoneuroendocrinology,* 28, 916-931, 2003 for more technical details). Other usable and generally accepted parameters of endocrine responsiveness are highest post-stress value; average post-stress value's; percentage post-stress increase (over rest, pre-stress, or baseline values); or net post-stress increase (over rest, pre-stress, or baseline values, e.g. $H^{stress}$-$H^{rest}$)

The stress response will never cause the individual parameters to reach a stable level, but instead the continuous measurements of the parameters will show a response that initially will lead to a peak level (either positive, or negative), which then will slowly return to normal (rest) levels, either because the stress trigger is gone or because habituation to the stress trigger would occur. These recovery values are described as: $S^{rec}$, $P^{rec}$, and $H^{rec}$. Ideally, the stress reactivity measurement is taken at (more or less) the moment of the peak level of the response, but any elevated level (or, when the effect would be a decrease, any diminished level) of the parameter could already bring the desired result. Generally all parameters have more or less defined recovery times, typically in the minutes range for the autonomic parameters (S, P), while hormonal parameters need more time to return to rest or baseline values.

The session could be closed by returning again to the rest situation and repeating the first (rest) measurements, but this is entirely optional and not per se required for a reliable quantification for the risk to obtain stress related (pathological) disorders like mood disorders, fatigue, or burnout.

Advantageously, as the production of associated hormones has a well-defined temporal delay, only after the stress response the hormone measurements should be repeated (e.g. multiple times in an period of 10 to 15 minutes) and/or estimated using valid methodology (e.g. derived on other assessments), and compared with the measurements from the resting period before the stressor was presented.

The actual prediction will be made by checking whether or not a predicted value that is calculated on basis of two of the three parameters can be confirmed by the actual measured value. For this step in the method of the invention first comparison data should be obtained from a number of control subjects. Ideally, these subjects should match the test subjects with respect to age, gender, ethnical characteristics, etc. The more similar to the test subjects and the larger the control group, the more reliable results can be obtained from the method of the present invention.

In order to obtain control parameter values from a control group it is preferred to apply a standardized stress stimulus, such as a standard physical exercise or psychological stimulus (e.g. specific standardized cognitive tasks, or (simulated) inter-personal challenges, like public performance or argumentation). Use of a standardize stress stimulus decreases the variability in the correlation between the three parameters and enables a more reliable prediction.

If the control group consists of healthy persons, i.e. persons that do not suffer from a mood related disorder or who are not at risk of obtaining a mood related disorder, the estimated value of the third parameter will reflect a state of no disorder or not at risk of a disorder. If the control group consists of persons that are already suffering from a mood related disorder, the estimated value of the third parameter will reflect a state of mood disorder.

The calculation of the estimation of the third parameters is performed on basis of the other two parameters. Depending on the nature of the parameters that are used a formula can be derived from the control data that defines the relation between the parameters.

The stress response of each parameter is obtained by taking the ratio or difference between the values measured in step a) and the values measured in step c): $R^s_{1..n}=S_1^{stress}/S_1^{rest} \ldots S_n^{stress}/S_n^{rest}$, $R^P_{1..n}=P_1^{stress}/P_1^{rest} \ldots P_n^{stress}/P_n^{rest}$, $R^h_{1..n}=H_1^{stress}/H_1^{rest} \ldots H_n^{stress}/H_n^{rest}$.

The stress score R for hormonal parameters may also be obtained by taking the value of the area under the curve (AUC) of the hormonal response during a period of 20 minute following the stress response.

The algorithm or formula to calculate the risk of obtaining a stress related mood disorder is relatively simple, but accuracy will depend on the (reliability of the) parameters(s) that has (have) been measured. In a general form the formula may be given as:

The stress risk score (A) can be assessed according to the following formula $$A = \text{Constant} + \text{Coefficient}_1 * R^H +/- \text{Coefficient}_2 * R^P +/- \text{Coefficient}_3 * R^S$$

in which the constant is based on the control population, and the consecutive coefficients on the used parameters and also in respect of the control population. Using this method of the invention confidence intervals (reliability of the estimated or calculated mood, anxiety, stress, or alike scores) are based on validation of the coefficients in the used population: these principles generally apply, though coefficients may differ for different populations (e.g. dependent on age, gender, specific preselected populations, e.g. suffering from stress symptoms).

As a practical example, for the parameters of cortisol concentrations, skin conductance ($R^S$) and Inter Beat Interval derived Heart Rate Variability ($R^P$, HRV) in response to mild mental/emotional stressors the following relation has been established (e.g. with regards to stress related disease risk:

Stress Risk Score

A: 2.3*[$HRV^{stress}$–$HRV^{rest}$]+0.1[Skin Conductance$^{stress}$–Skin Conductance$^{rest}$]

This means that for a control group of persons suffering from a mood related disorder or having a risk to develop a mood based disorder, the hormonal concentration can be estimated from the parameters of skin conductance and HRV in the following way:

$$\text{Cortisol conc}^{estimated} = 2.3*[HRV^{stress}-HRV^{rest}]+0.1 \\ [\text{Skin Conductance}^{stress}-\text{Skin Conductance}^{rest}].$$

A third step in the prediction of the risk on a mood related disorder will then be to compare the estimated value of the third parameter with the actually measured third parameter. If these are nearly identical (or lying within the confidence range that has been established for the control group), the conclusion should be drawn that the tested person should fall within the same category as the control group. If the value falls outside this confidentiality interval and/or if the actually measured value differs very from the estimated value, the conclusion should be drawn that the tested person is very unlike the control group.

It should be clear from the above example that any of the three parameters may act as the estimated parameter, as long as the other two parameters are measured. However, for practical reasons, a preferred choice for the parameter to be estimated is the hormonal parameter.

Additionally, if data including the hormonal response is real time recorded and/or stored the presence of a stressor can be retrospectively concluded within 10 to 15 minutes after an 'incident'. If the sympathetic or parasympathetic response is indeed followed by a significant hormonal response, a significant stressor must have been present. Using the present invention in this way it may allow to monitor, measure or quantify the number of stressors and their overall impact on health and performance over for example a working day (e.g. in office, as a truck driver, or other). In this way feedback can be provided reasonably quickly (e.g. as biofeedback within half an hour), or more cumulative (e.g. over a working day of say 8 hours).

The found correlation between the parasympathetic, sympathetic and hormonal parameter of the present invention can also be used for continuously assessing the stress level of a person. In such a method only two of the three parameters need to be measured, since the third parameter can be estimated on basis of the control population. Such a method would be especially suited to detect stressful events, which can be useful in methods for assessing norm data for work load or work pressure or to investigate the level of stress that occurs during specific tasks (such as driving a car, sport playing or sitting exams).

Such a method can be used in relation to established norm-data for specific populations, e.g. to monitor specifically defined populations with an established higher risk (e.g. recurrent depressive episodes, sequential absences due to unknown/unclear causes, panic attacks, and the like):—

The whole series of measurements (together with administration of the stress stimulus) can be performed in a controlled environment, such as a hospital or at a doctor's office. In such an environment a standardized way of measuring the parameters with professionalized equipment can be accomplished. It would be possible that the data of the measurements are fed directly into a system that can be used not only to store these data, but also to perform the necessary calculations and to provide the desired prediction. With current developments in ambulatory hardware (e.g. smart watches, bands around chest or thorax, ever more advanced measurement scale, others), IT infrastructures (e.g. blue tooth, wifi) and interfaces (smartphones, app's, ambulatory e.g. laptop or tablet based applications, others) the necessary parameters can be assessed ever more reliably in a more ambulatory environment, rendering the present invention applicable in the more preventive arena's like employability, coaching, lifestyle support, etc.

A standardized stressor can be applied in these contexts as well (e.g. cognitive tasks, mental arithmetic, public performance, others). Further, with continuous monitoring it can be established retrospectively or in real time if the person using this method encountered stressors, e.g. during a working day, in traffic, in school, or otherwise. By simply continuously monitoring and comparing with the data for the representative population (e.g. employees, truck drivers, students, others) and calculating what score comes out the stress level of the test person can be monitored continuously. When sufficient connectivity and data storage may be available this can advantageously be done real time.

This last application based on the present invention can easily be combined with feedback to the test person to warn for critical levels of stress and/or excitement, e.g. by means of a sound, tremor (e.g. via smartwatch), alert, changing colors on a display, or otherwise.

The present invention is also directed to a system comprising one or more devices for measurement of at least two parameters selected from at least one sympathetic parameter, at least one parasympathetic parameter and one hormonal parameter, further comprising a unit able to process an algorithm for performing a method according to the invention.

Accordingly, the present invention also comprises a system for controlling and assisting the screening for, prediction or diagnosis of stress and related disorders.

Central in this system would be a calculation unit for performing the actual calculations as discussed above. To this end, the calculation unit would receive input from a storage device for obtaining stored parameter values or directly from measuring devices that on- or offline will provide these parameter values. A management module may be provided for input-output of the system, for calibration and set-up of the system and/or for entering further relevant data, such as the nature (name, age/day of birth, etc.) of the test subject, the date and time of the test (could be done automatically) and the individual measurements, the parameters measured and any further data that would be advantageous to store or use with the results of the measurements. This also means that the storage device will not only have an output to the calculation unit, but also an input for receiving data and parameter values to be stored. Such a data storage facility (also indicated as memory) may be in any form of digital storage of data, such as a disk, a cd-rom, a USB-stick, a memory card and the like, or a connection to an online data storage facility (e.g. cloud- or server based). The memory will be accessible by and may be part of the processor or controller.

The term "module" or "unit" as in management module or calculation unit is used to indicate the modular character of the units that make up the system. In other, words, the functionality of the system may be broken up into units, which either represent a function or a (hard- or software) embodiment and which functions may be combined if needed.

As indicated, the system will have a management module that would comprise a user interface. The term "user interface" may comprise one or more hardware elements configured to perform operational acts in accordance with the present system and method, such as to provide for input of additional data, to control the flow and timeliness of the parameter measurements, and the like. The user interface, the calculation unit, the management module and other components of the system may be connected to and/or controlled by a processor, which processor may be a dedicated processor for the current system or may be a general-purpose processor which may only be partly dedicated for serving in the system described herein. The processor may use a program portion, multiple program segments or may be a hardware device using a dedicated multi-purpose integrated circuit. Any type of processor may be used, such as a dedicated one or a shared one. The processor may include micro-controllers, central processing units (CPUs), digital signal processors (DSPs), ASICs or any other device that is capable of performing the same functions.

In a particular embodiment, the system will comprise a processor connected to or having access to a network, to which system one or more clinical measuring devices are added, which can be operated by the user (either the test person or a person that is conducting an assessment). Said processor will contain software to analyze the measurements (check for correctness of data, possibly including calibration), an algorithm to process these data and further communication means, such as one or more screens. Also, the system will be able to retrieve earlier values for each test subject that can act as control for the measurements and or can be used to visualize a trend over time, calculate or present trend analytics and/or measure or monitor the development of stress state, associated disease, intervention, or therapy.

The system will preferably comprise a screen for the output of the measurements or, preferably, for the output of an indication about the stress status of the subject. This may be accompanied by an alarm setting that becomes active (e.g. sounding a buzzer or bell, or highlighting the status in a different color) when the stress situation changes and passes a pre-set condition. Alternatively, the alarm signal will only be used as a signal to be stored. If the system is used to monitor the stress situation over time of an individual it will be easy to just add the total 'alarm time' or the number of occurrences that the alarm signal has been triggered.

It is also possible and especially advantageous for portable systems or devices for continuous measurements to continuously monitor only one simple sympathetic or parasympathetic parameter (e.g. skin conductance) and to start measuring all necessary parameters once this single monitored parameter has passed a pre-set level. In this way one is confident to measure all occurrences of possible stressful events while maximally saving energy and/or batteries.

In the system of the invention one or more clinical (or more commercially available) measuring devices can be present and normally a first choice will consist of one or more devices selected from the group of a device for reliably measuring heart rate and parameters derived from heart rate and/or ECG, a device for measuring blood pressure, a device for measuring respiration, technology (electrodes or others) to assess skin conductance levels (being a dominantly sympathetic parameter), a device to measure skin temperature, such as a skin infrared thermometer; devices to either estimate or assess changes in hormonal concentration etc. Such devices or means may comprise electrodes in precordial/thoracic lead, classical methods of blood-pressure measurement, thoracic bands containing one or more electrodes, stick on electrodes and the like. In a specifically preferred embodiment, the device is a smartwatch in which measurements of the sympathetic and parasympathetic parameters are performed by e.g. measurement of heart rate variables, skin conductance, etc, at the site of the watch, i.e. at the wrist. It is even possible, nowadays, to measure such parameters with a non-invasive technology, such as impedance plethysmography or photoplethysmography with which results are obtained that would be useful in the present system (Schafer and Vagedes, Int. J. Cardiol. 166:15-29, 2013).

For measurements of hormone concentrations, e.g. corticosteroid, e.g. samples of saliva, blood may be taken, but measurements can also be conducted via the skin or other, reliable, means. If necessary and in a more clinical context saliva samples can for example be collected every 5 or 10 minutes during a standardized protocol, being sent to an analytical facility and values being input manually to perform the necessary calculations. However, current developments in hardware seem to provide the opportunity to do such analytics at the Point of Care (PoC) more or less real-time in conjuncture (and partly automated) with the assessment of ANS reactivity. Depending on the parameters that will be measured by these devices, the devices may be relatively simple, like a digital watch that can measure heart rate to very sophisticated ECG recording apparatuses.

For determining the hormone levels either a blood sample can be taken by the subject (e.g. by puncturing one of the fingers and applying a drop of blood on a test plate); or saliva samples can be used (e.g. by means of so called 'salivettes'); while new technologies are being developed to make such analytics Point of Care (e.g. by antibodies on a test-strip, via optical means, or other), what can reasonably be expected to provide more comfortable, well timed (e.g. in relation to ANS reactivity) and nevertheless reliable & valid measurements. Any assay that would reveal a quantitative measure of the blood hormones may be used. For methods to quantify salivary cortisol, see e.g. Shirtcliff, et al., Clin Ther. 2015; 37(3): 505-514 who report the development and testing of a system capable of measuring salivary cortisol within 20 minutes of sample collection. The system involves a saliva collection device, a lateral flow test strip, and a fluorescent LFA cassette reader to quantify cortisol. When the system was compared against ELISA for cortisol quantification, good agreement was found ($r=0.8$) and parameters were within physiological range. The reader conveniently connects to smartphone via Bluetooth and is portable, yet it remains quite large. Assay strips and the reader are commercially available. Also Zangheri, M., Biosens Bioelectron. 2015, 15; 64:63-8 developed a chemiluminescent imaging system to quantify cortisol in human saliva using a LFIA with the analytical membrane enclosed in a cartridge that is placed in a smartphone adapter in front of the smartphone camera. The method is simple and relatively fast (30 min.), provides values within the physiological range (DR: 0.3-60 ng/mL) and there was good agreement with ELISA results.

All such technologies are (generally combined) useful to operate the given algorithms and as such, when handled accurately, should be able to present the relevant risk scores, or fairly reliable estimates of any given missing variable if all others can be quantified (mood/psychopathological state, hormonal responses, sympathetic responses, or parasympathetic responses).

Estimation of one of the three parameters from the other two parameters—even without comparing this estimated parameter with actually measured values—can be very valuable in (psychiatric) practice. In case that a patient is already diagnosed as scoring high on anxiety or burn-out, measuring of only the sympathic and parasympathic parameter (which can be easily done when visiting a medical practitioner) and estimate the value of the hormonal parameter from that can already assist with the risk assessment for that patient.

In one special case, for patients that have an adrenal disorder, this estimate can be very relevant. For those patients that are not able to produce cortisol run the risk to develop a so-called Addison's crisis due to a stressing event. Using the estimation of the hormonal parameter as provided for in the present application, it is possible to calculate the dosis of cortisol that normally is produced. Administration of such a dosis of cortisol to said patient very shortly after the stressful event can then be a life-saving action.

The presence of a central database provides for the possibility that the data that are comprised in there can be used for demographic studies or other statistical analyses. This may result in upgrades of the used algorithms One use for such a central database in the current invention is the collection of data from control subjects to use these as control data for later individual measurements. It shall be easily understandable that demographic studies with these data could then again be used to improve the performance of the methods and system of the invention, e.g. by optimizing the measuring frequency, or by adjusting thresholds for alarm. Further, the central database provides a source of data on the progress of stress related disorders and further prediction algorithms can be derived from such data.

Example 1 is Comparing Mathematical Algorithms to Quantify Stress

Example 1 response patterns using diverse measurement technologies independently though streaming the data to a centralized location for processing and analytics:

30 professional truck drivers (29 male, 1 female, 43±13 years and 91±17 kg) were equipped with a Discrete Tension Indicator (DTI) device. DTI is a wrist wearable device with integrated sensors to record skin conductance, skin temperature, ambient temperature, ambient light and 3-dimensional accelerometer data. The sensor data can be streamed live to receiving station via. Bluetooth link. The sensor data for the skin conductance was sampled at 10 Hz and it has the an operating range of 0.01-0.65 micro Siemens with sensitivity of 0.001 micro Siemens. Collected data were transmitted to PC. Philips N.V. developed a method to derive Estimated Cortisol Response from skin conductance responses (EP2747638, which is also included in this sensor/device. The physiological responses were extended by a yet independently applied Philips A3 OHR sensor (heart rate monitor), used to derive HRV components as well.

The participants were subjected to a driving simulator test during which test they were asked to perform stress-inducing tasks. Each subject was asked twice, to count from 1-60 as a moderate stress activity with some interval between the two moderate stress activities. Likewise, backward counting from some random number is used as a high stressor, where driver was asked to complete the count within 7 seconds and after that asked to count backward again from another random number; this process was repeated for 317 seconds. The length of the stress simulation task was 25 minutes and every participant went through health check-up to avoid collection of data from unhealthy subjects (exclusion criterion). (see Table 1).

Skin conductance (SC) was monitored and after discarding test results that were not useful for technical reasons, results for 19 test persons remained useful. The 25 minutes signal was divided into segments of 10 seconds and for every segment the average level of the signal was determined. SC varies from person to person and depends on several factors, like age, gender, diet and sleep etc. [Picard et al., IEEE Trans. Pattern Anal. Mach. Intell. 23:1175-1191, 2001]]. To minimize the effect of SC variation, mean normalization was applied on the dataset of each driver individually. FIG. 5 illustrates the average SC signal of all drivers after applying mean normalization. The first black line shows start of first moderate stress activity and second line represents end of second moderate task. Whereas, the red lines represent start and end of high stress task. Additionally, applying the method disclosed in EP2747638, the DTI device was capable of providing an Estimated Area under de Cortisol (EAC) curve following this initial sympathetic arousal (as indicated by the significant SC response) t Based on previous work (e.g. Westenberg et al., 2009, unpublished findings) the following routines were applied to construct accurate stress identifying algorithms The SC, EAC, and (independently collected by means of the Philips A3 OHR sensor) HR/HRV data were filtered, processed and fed into various machine learning algorithms such as support vector machines, random forests, gradient boosting, K-Nearest Neighbours, Logistic Regression and Naïve Bayes. In this study the data from the algorithms were evaluated using leave one out cross validation (LOOCV) and compared (A. Saeed, December 2017, Twente University, NL). It was found that on the present data the Support vector machines method implementing SC and EAC data was the most predictive for establishing stressful accuracies of 83 to 91% (see Table 2). Addition of the HRV data made the prognostic models even more accurate (unpublished results), with higher accuracies and lower standard deviations/confidence intervals.

Example 2 Smartwatch

Following these results a prototype smartwatch suitable for measuring the required physiological/endocrine parameters to be used for predicting stress in accordance with the invention was built (see also FIG. 5). The below Table summarizes the features shown in FIG. 5 and their function (BLE=Bluetooth Low Energy). Because other features were part of the original requirements (for other reasons), more technologies were involved than strictly necessary to apply the method of the present invention.

| Features | Description |
| --- | --- |
| Buttons | 2x buttons for controlling device UI and reset/power off functionality |
| Display for rendering | Display for using certain data elements on UI and Device status info, like battery and BLE connection status |
| Skin temperature measurement | Skin temperature measurement from user's wrist. The measurement resolution is preferred to be around ~0.1 degrees. |
| Heart rate measurement | Philips A3 OHR sensor |
| Accelerometer measurement | Primary use of accelerometer is to capture the users motion data |
| Skin conductance measurement | Skin conductance sensor sends raw sensor data which is needed for further analysis to measure user's excitement and stress levels |
| Charging | USB charger was selected as charging interface. Battery charging indication and levels on UI. |
| Rechargeable Battery | Minimum 24 hours usage time for the wearable with following use case: All sensors (accelerometer, OHR, Skin conductance, Skin temperature) measurements taken and sent out through BLE 12 hours All sensors data measurements taken and stored to file system 12 hours In addition to this, it is expected UI notifications (some with vibra) and UI usage ~50 × 10 sec periods |

The Core processor is an nRF52832 SoC, which is a powerful, highly flexible ultra-low power multiprotocol SoC ideally suited for Bluetooth® Smart. ANT and 2.4 GHz ultra low-power wireless applications from Nordic Semiconductor. This processor is equipped with software instructions which are able to accommodate the measurement of the parameters as indicated in the present invention and the processing and calculations as provide in the claimed methods.

The UI is a display, such as the Futaba white Mono Color OLED (EPW0702AB), 128×96, dot matrix OLED segment. This display will show basic information like time, battery level, Bluetooth connectivity and simple parameters, like heart rate or skin conductance.

The device will provide for a data storage module, such as an internal flash memory (preferably-a 2 Gbit NOR flash). Preferably, the device contains a vibration motor to provide for alerts and notifications to the wearer of the device.

Sensors for the measurement of the parameters are commercially available and preferred are a Philips A3 OHR sensor (heart rate monitor and accelerometer sensor) and a Philips WeST (Wearable Sensing Technologies) Skin conductance sensor. Further the device may contain a skin infrared thermometer.

From a mechanical point of view, the wearable smartwatch consists of a main module which includes the display and buttons, one or more batteries, the OHR sensor, a skin temperature sensor, a back cover and skin conductance pads. This structure is then completed by wrist bands connected to the main module which enable wearing of the device around the wrist (FIG. 6)

TABLE 1

Stress activity breakdown in the truck drivers study testing the proposed stress identifying algorithms/methods

| Period | Stress label | Approximate duration |
|---|---|---|
| Normal driving | 0 | 905 s |
| Instructions | N/A | 8 s |
| Counting 1-60 | 1 | 28 s |
| Instructions | N/A | 8 s |
| Normal driving | 0 | 23 s |
| Instructions | N/A | 8 s |
| Counting 1-60 | 1 | 28 s |
| Instructions | N/A | 8 s |
| Normal driving | 0 | 52 s |
| Instructions and countdown | N/A | 53 s |
| Counting backwards in 7s (including all instruction for new starting numbers) | 2 | 317 s |
| Instructions | N/A | 8 s |
| Normal driving | 0 | 57 s |
| Instructions | N/A | 8 s |
| Total duration of driving | | 1511 s |

TABLE 2

Confusion matrix for binary stress classification using SVM, n is the number of windows (of 300 seconds) that is used for both training the classifier and making the prediction (A. Saeed, December 2017, Twente University).

| n = 2566 | Predicted: No Stress | Predicted: Stress |
|---|---|---|
| Actual: No Stress | 1908 | 59 |
| Actual: Stress | 167 | 432 |

Examples 3 & 4: identifying youth at risk.

Further analyzing data, for example described in Westenberg et al. (2009, Biological Psychology), showed a significant difference in response patterns between (general healthy) youth scoring low-to-average on anxiety and depression symptoms, versus there aged matched peers scoring significantly higher on standardized assessment methods for anxiety and depression (example 3). The participants scoring above average on depressive and anxious symptoms showed a stress response pattern as described in this invention, indicating a neurobiological stress response profile indicative for proneness for stress related health outcomes. For example more prominent depressive or anxiety related symptoms developing over time, potentially leading to full blown (psychiatric) syndromes. These findings are in line with Kallen, 2007 (Chapter 6), presenting data in 99 youths suffering from anxiety disorders (with or without depressive symptoms) (example 4). The study describes the combination of sympathetic arousal and an increased cortisol response to stress is directly related to self-reported anxiety scores. Again the contribution of HRV (quantified using frequency based methods: high frequency power of inter-beat-interval changes over time), is in this population present thought less proportional (like in the truckdrivers, example 1). The thus constructed prediction models appeared to be able to accurately discriminate 'high risk' individuals from their low risk peers (general population: Westenberg et al., 2009; clinical population in relation to the severity of syndromes: Kallen 2007).

Both Westenberg et al. (2009) and Kallen (2007) use more or less the same, generally known and applied methodologies to measure stress responses in an laboratory ('controlled') environment: Salivettes to collect saliva samples for cortisol measurements, executed in a clinical laboratory; precordial placed electrodes for HR/HRV; and Ag/AgCl electrodes on the middle phalanx of the ring and index finger for SC. Consequently, the described invention can be applied using (a combination of) less sophisticated assessment technologies, other than wristwatches specifically designed according to the present specifications.

The invention claimed is:

1. A method for warning a person of critical levels of stress or excitement, said method comprising; a) Measuring at least three parameters for the person comprising at least one sympathetic, one parasympathetic and one hormonal parameter during a stress response, said result of the measurement depicted as Rs, Rp and Rh respectively; b) Estimating the value of one of the parameters of step a) based on the other two parameters; c) Comparing the estimated value of one of the parameters of step b) with the measured value of step a) of the same parameter; d) Determining whether the measured value of step a) is substantially identical with the estimated value from step b) thereby indicating said critical levels of stress or excitement for the person; and e) Warning the person of said critical levels of stress or excitement, wherein the person obtains treatment to address said critical levels of stress or excitement.

2. The method according to claim 1, wherein the measurement during a stress response in step a) is performed according to a method comprising the steps of:
  a1) measuring during rest condition the at least three parameters, comprising the at least one sympathetic parameter, said parameter being a parameter related to the sympathetic autonomic nervous system (S1rest . . . Snrest, in which n is the number of parameters), at least one parasympathetic parameter, said parameter being related to the parasympathetic autonomic nervous system (P1rest . . . Pnrest, in which n is the number of parameters) and the at least one hormonal parameter, said parameter being related to the hormonal system of the hypothalamus-pituitary gland—adrenal (HPA) axis (H1rest . . . Hnrest, in which n is the number of parameters);
  a2) applying a stress stimulus resulting in a stress condition;

a3) measuring said at least three parameters measured in step a1) during the stress condition (S1 stress ... Snstress; P1 stress ... Pnstress; H1 stress ... Hnstress;) and a4) calculating the stress response of each parameter by taking the ratio between the values measured in step a) and the values measured in step a3): Rs1 ... n=S1stress/S1rest ... Snstress/Snrest, Rp 1 ... n=P1 stress/P1rest Pnstress/Pnrest, Rh 1 ... n=H1 stress/H1rest ... Hnstress/Hnrest.

3. The method according to claim 2, wherein the stress stimulus is a standardized stress stimulus.

4. The method according to claim 1, wherein the estimating in step b) is achieved by a method comprising the steps of b1) comparing the values of two of said at least three measured parameters with averaged data taken from a normal control group, to find values that closely resemble the values measured; and b2) taking the value of the third parameter that belongs to the averaged normal control data as the estimated value of the third parameter.

5. The method according to claim 1, wherein the estimated value is for the hormonal parameter.

6. The method according to claim 1, wherein the at least one parameter relating to the sympathetic autonomic nervous system is chosen from the group consisting of Skin Conductance (SC), pupil dilatation, and specified derivatives of blood pressure, such as low/mid frequency power, reflecting changes over time in frequencies between 0.7 and 0.15 Hz, of Systolic Blood Pressure.

7. The method according to claim 1, wherein the at least one parameter relating to the parasympathetic autonomous nerve system is chosen from the group consisting of heart rate derivatives, quantifiable as the root Mean Square of Successive interbeat-interval Differences (RMSSD), or the High Frequency power of the Heart Rate power spectrum.

8. The method according to claim 1, wherein the at least one hormonal parameter is chosen from the group consisting of a concentration of cortisol, ACTH, CRF, vasopressin or adrenalin of said person is measured in a saliva, blood or urine sample, or via the skin or optical methods.

9. A system configured to carrying out the method according to claim 1, said system comprising one or more sensors configured to measure the at least one sympathetic parameter, the at least one parasympathetic parameter and the one hormonal parameter, said system further comprising a processor configured to: a) Measure the at least one sympathetic parameter, the at least one parasympathetic parameter and the one hormonal parameter during a stress response, said result of the measurement depicted as Rs, Rp and Rh respectively; b) Estimate the value of one of the parameters of step a) based on the other two parameters; c) Compare the estimated value of one of the parameters of step b) with the measured value of step a) of the same parameter; d) Determine whether the measured value of step a) is substantially identical with the estimated value from step b) thereby indicating said critical levels of stress or excitement for the person; and e) Warn the person of said critical levels of said stress or excitement, wherein the person obtains treatment to address said critical levels of stress or excitement; said system further comprising an alarm configured to become activated when the measured value of a parameter is substantially identical with the estimated value of the same parameter.

10. The system according to claim 9, wherein said system is a portable system.

11. The system according to claim 10, wherein said portable system is a wristwatch.

12. The system according to claim 9, wherein said system has an output means.

13. The system according to claim 9, wherein said system comprises a storage means for storing of the measured data.

14. The system according to claim 9, wherein said measurement sensors and said processor are remote from each other and are able to communicate data or instructions with each other.

15. The system according to claim 9, wherein the processor and at least one measuring sensor are housed a same housing.

16. The system according to claim 9, wherein the one or more sensors are configured to measure at least one of heart rate, blood pressure, breathing rhythm, concentration of cortisol, ACTH, CRF, adrenalin or vasopressin.

17. The system according to claim 9, comprising at least one sensor configured to measure heart rate variability, at least one sensor configured to measure skin conductance and a sensor configured to measure a hormonal parameter.

18. The system according to claim 17, wherein the hormonal parameter is cortisol.

19. The system according to claim 17, wherein the processor is configured to estimate a value of the hormonal parameter based on the heart rate variability and the skin conductance.

20. The system according to claim 9, comprising at least one sensor configured to measure heart rate variability and skin conductance and a sensor configured to measure a hormonal parameter.

21. The system according to claim 20, wherein the hormonal parameter is cortisol.

22. The system according to claim 20, wherein the processor is configured to estimate a value of the hormonal parameter based on the heart rate variability and the skin conductance.

* * * * *